(12) United States Patent
Litzler et al.

(10) Patent No.: US 8,545,255 B2
(45) Date of Patent: Oct. 1, 2013

(54) SUBCUTANEOUS DEVICE FOR ELECTRICAL PERCUTANEOUS CONNECTION

(75) Inventors: Pierre-Yves Litzler, Saint Martin du Vivier (FR); Pierre Sabin, Paris (FR)

(73) Assignee: Centre Hospitalier Universitaire de Rouen, Rouen (FR)

( * ) Notice: Subject to any disclaimer, the term of this patent is extended or adjusted under 35 U.S.C. 154(b) by 176 days.

(21) Appl. No.: 13/265,838

(22) PCT Filed: Apr. 23, 2010

(86) PCT No.: PCT/EP2010/055430
§ 371 (c)(1),
(2), (4) Date: Oct. 21, 2011

(87) PCT Pub. No.: WO2010/122142
PCT Pub. Date: Oct. 28, 2010

(65) Prior Publication Data
US 2012/0045918 A1    Feb. 23, 2012

(30) Foreign Application Priority Data
Apr. 23, 2009  (FR) .................................. 09 52661

(51) Int. Cl.
*H01R 4/24*  (2006.01)
*A61N 1/00*  (2006.01)

(52) U.S. Cl.
USPC .................. 439/426; 607/36; 607/37; 607/38

(58) Field of Classification Search
USPC ................... 439/426, 178, 179, 909, 86, 271, 439/289; 607/36–38
See application file for complete search history.

(56) References Cited

U.S. PATENT DOCUMENTS

| 301,655 A | * | 7/1884 | Young ........................... 307/112 |
| 663,750 A | * | 12/1900 | Greil ............................. 439/426 |

(Continued)

FOREIGN PATENT DOCUMENTS

| DE | 8617583 | 8/1986 |
| EP | 0 280 301 | 8/1988 |

(Continued)

OTHER PUBLICATIONS

P. Sabin et al., Permanent percutaneous electrical connection. General principles, Rev Laryngol Otol Rhinol. 1997, pp. 335-342.

(Continued)

*Primary Examiner* — Amy Cohen Johnson
*Assistant Examiner* — Vladimir Imas
(74) *Attorney, Agent, or Firm* — Blakely Sokoloff Taylor & Zafman

(57) ABSTRACT

The invention concerns an electrical connection system for a percutaneous electrical connection between an electrical device (2) inside an animal body and an electrical device (3) outside said body, comprising a subcutaneous device (10) designed to be connected to internal electrical device (2), said subcutaneous device (10) comprising:

- an open housing (11) having at least one inner compartment (12), said compartment (12) being filled with a conductive material into which an electrical connection plug can be inserted, the conductive material of compartment (12) being further connected to connection means (5) designed to be connected to internal electrical device (2);
- a sealing membrane (13) for sealing housing (11), said sealing membrane (13) being formed of an insulating and flexible material designed for insertion of electrical connection plugs from outside housing (11) through said sealing membrane (13) to the conductive material of compartment (12);

characterized in that housing (11) comprises alignment means (14) to facilitate positioning and to guide the insertion of electrical connection plugs into the corresponding conductive materials.

18 Claims, 3 Drawing Sheets

(56) References Cited

U.S. PATENT DOCUMENTS

| | | | |
|---|---|---|---|
| RE11,969 E * | 2/1902 | Greil | 439/426 |
| RE11,970 E * | 2/1902 | Greil | 439/426 |
| 697,856 A * | 4/1902 | Lefebre | 439/426 |
| 2,858,518 A * | 10/1958 | Chrystie et al. | 439/426 |
| 3,158,420 A * | 11/1964 | Olson et al. | 439/390 |
| 3,230,495 A * | 1/1966 | Warwick et al. | 439/179 |
| 3,522,576 A * | 8/1970 | Cairns | 439/201 |
| 3,527,220 A * | 9/1970 | Summers | 604/153 |
| 3,675,062 A * | 7/1972 | Flasche | 313/365 |
| 3,731,669 A * | 5/1973 | Fitzgerald | 600/20 |
| 3,750,194 A * | 8/1973 | Summers | 623/23.66 |
| 3,924,639 A * | 12/1975 | Hess | 607/122 |
| 4,004,843 A * | 1/1977 | Boenning et al. | 439/86 |
| 4,220,386 A * | 9/1980 | Kenny | 439/86 |
| 4,402,560 A * | 9/1983 | Swainbank | 439/37 |
| 4,411,276 A | 10/1983 | Dickhudt et al. | |
| 4,425,017 A * | 1/1984 | Chan | 439/276 |
| 4,516,820 A * | 5/1985 | Kuzma | 439/289 |
| 4,824,390 A * | 4/1989 | Crane et al. | 439/271 |
| RE32,947 E | 6/1989 | Dormer et al. | |
| 4,934,366 A | 6/1990 | Truex et al. | |
| 4,941,472 A | 7/1990 | Moden et al. | |
| 4,954,105 A | 9/1990 | Fischer | |
| 5,004,897 A * | 4/1991 | Biggio et al. | 235/441 |
| 5,017,153 A * | 5/1991 | Bowman | 439/426 |
| 5,095,903 A | 3/1992 | DeBellis | |
| 5,131,854 A * | 7/1992 | Jose et al. | 439/86 |
| 5,273,449 A * | 12/1993 | Mattis et al. | 439/201 |
| 5,358,409 A * | 10/1994 | Obara | 439/20 |
| 5,360,350 A * | 11/1994 | Koblitz et al. | 439/276 |
| 5,427,547 A * | 6/1995 | Shimirak et al. | 439/521 |
| 5,489,215 A * | 2/1996 | Wright | 439/86 |
| 5,562,491 A * | 10/1996 | Shimirak et al. | 439/521 |
| 5,571,148 A * | 11/1996 | Loeb et al. | 607/57 |
| 5,580,265 A * | 12/1996 | Koblitz et al. | 439/276 |
| 5,645,442 A * | 7/1997 | Cairns | 439/201 |
| 5,679,026 A * | 10/1997 | Fain et al. | 439/651 |
| 5,701,895 A * | 12/1997 | Prutchi et al. | 600/300 |
| 5,782,645 A * | 7/1998 | Stobie et al. | 439/289 |
| 5,807,144 A * | 9/1998 | Sivard | 439/816 |
| 5,855,494 A | 1/1999 | Blaszczyk et al. | |
| 5,919,213 A | 7/1999 | Nelson et al. | |
| 5,954,058 A * | 9/1999 | Flaherty | 128/899 |
| 6,038,481 A * | 3/2000 | Werner et al. | 607/119 |
| 6,043,273 A | 3/2000 | Duhaylongsod | |
| 6,070,103 A | 5/2000 | Ogden | |
| 6,280,243 B1 | 8/2001 | Liu et al. | |
| 6,287,275 B1 * | 9/2001 | Atala | 604/28 |
| 6,321,126 B1 * | 11/2001 | Kuzma | 607/137 |
| 6,324,416 B1 * | 11/2001 | Seibert | 600/386 |
| 6,540,549 B2 | 4/2003 | Rupert | |
| 6,790,077 B1 | 9/2004 | Chen | |
| 7,004,787 B2 | 2/2006 | Milan | |
| 7,225,028 B2 * | 5/2007 | Della Santina et al. | 607/57 |
| 7,252,542 B2 | 8/2007 | Chen | |
| 7,347,751 B2 * | 3/2008 | Sweeney et al. | 607/119 |
| 7,488,187 B2 | 2/2009 | Wolf | |
| 7,494,370 B2 | 2/2009 | Chang et al. | |
| 7,534,127 B2 * | 5/2009 | Parker et al. | 439/425 |
| 7,648,401 B2 * | 1/2010 | Guenther et al. | 439/669 |
| 7,794,256 B1 * | 9/2010 | Sochor | 439/289 |
| 7,803,021 B1 | 9/2010 | Brase | |
| 7,917,218 B2 * | 3/2011 | Iyer et al. | 607/36 |
| 8,079,846 B1 | 12/2011 | Cookson | |
| 8,109,792 B2 | 2/2012 | Briano et al. | |
| 8,126,557 B2 * | 2/2012 | Jang et al. | 607/37 |
| 8,233,986 B2 * | 7/2012 | Deininger et al. | 607/37 |
| 8,251,731 B2 * | 8/2012 | Boyd et al. | 439/347 |
| 2003/0167077 A1 * | 9/2003 | Blamey et al. | 607/57 |
| 2006/0058731 A1 * | 3/2006 | Burnett et al. | 604/29 |
| 2008/0208267 A1 | 8/2008 | Alexander et al. | |
| 2010/0331616 A1 * | 12/2010 | Forsell | 600/37 |
| 2011/0257577 A1 * | 10/2011 | Lane et al. | 604/6.11 |
| 2012/0028490 A1 * | 2/2012 | Litzler et al. | 439/278 |
| 2012/0059443 A1 * | 3/2012 | Sabin | 607/116 |
| 2012/0123337 A1 * | 5/2012 | Forsell | 604/151 |

FOREIGN PATENT DOCUMENTS

| | | |
|---|---|---|
| EP | 1 504 789 | 2/2005 |
| FR | 2568477 | 2/1986 |
| FR | 2 832 778 | 5/2003 |
| WO | WO 92/22107 | 12/1992 |
| WO | WO 98/57702 | 12/1998 |
| WO | WO 99/46002 | 9/1999 |
| WO | WO 03/092794 | 11/2003 |

OTHER PUBLICATIONS

P. Sabin et al., A new application for extra-oral implants: the permanent percutaneous electrical connection, 1999, pp. 123-131, Masson, Paris.

* cited by examiner

SUBCUTANEOUS DEVICE FOR ELECTRICAL PERCUTANEOUS CONNECTION

This is non-provisional application claiming the benefit of International application number PCT/EP2010/055430 filed Apr. 23, 2010.

FIELD OF THE INVENTION

The present invention concerns electrical connections in the medical field, and more particularly a system permitting a percutaneous electrical connection between a medical device implanted in the body of an animal, in particular in the human body, and an electrical device outside the body.

TECHNICAL BACKGROUND

The significant development of electrical equipment designed to be installed inside the patient's body to compensate for a defect in a natural organ, requires being able to transmit either the power required by this equipment from a power source outside the body to the inside of the body, or to collect electrical information originating from the defective natural organ and/or electrical equipment designed to compensate for these defects.

For this electrical implanted equipment, power is currently provided by three main methods. A first method consists of using implanted batteries that directly supply the electrical implanted medical devices. However, implanted batteries are insufficient to provide long lasting power, especially for implanted medical devices requiring substantial electrical power, such as implanted ventricular assist devices or total artificial hearts, to name only two applications concerning cardio-thoracic surgery.

Another solution is based on the principle of non-invasive transcutaneous electrical conduction, by induction or transmission of electromagnetic microwaves. Once again, this type of connection has limited possibilities for use and is therefore somewhat restricted, since the transfer of high power energy requires antennas of a size that are poorly compatible with a normal life.

The third method resides in percutaneous transmission, which allows connecting the electrical implanted medical device to an electrical device outside the patient, which has the advantage of offering more varied uses, especially for data transfer. Indeed, in addition to their power supply, more and more implanted devices transmit or receive a certain number of signals necessary or useful for their operation.

Such percutaneous transmission can be done directly by passing a cable through the skin, or by means of a permanent percutaneous electrical connection using a percutaneous implanted device (such as a socket) for an electrical connection between the inside and the outside of the patient's body.

A goal of the present invention is to propose a novel system permitting percutaneous electrical connection between an internal electrical device implanted in the body of an animal, in particular in a human being, and an external electrical device, such as, for example, a power source.

In particular, a goal of the present invention is to propose an electrical connection system for percutaneous connection that can be used as needed, without requiring a permanent connection with the external electrical device.

Another goal of the present invention is to propose an electrical connection system for a percutaneous connection that can be used as an emergency connection, to replace a defective main electrical connection, for example.

DISCLOSURE OF THE INVENTION

To this end, an electrical connection system is proposed for a percutaneous electrical connection between an electrical device inside an animal body and an electrical device outside said body, characterized in that it comprises a subcutaneous device designed to be connected to the internal electrical device, said subcutaneous device comprising:

- an open housing having at least one inner compartment, said compartment being filled with a conductive material into which an electrical connection plug can be inserted, the conductive material of the compartment being further connected to connection means designed to be connected to the internal electrical device;
- a sealing membrane for sealing the housing, said sealing membrane being formed of an insulating and flexible material designed for insertion of electrical connection plugs from outside the housing through said sealing membrane to the conductive material of the compartment.

Some preferred but non-limiting aspects of this electrical connection system, taken alone or in combination, are the following:

- the housing comprises several inner compartments insulated electrically from one another, each compartment being filled with a conductive material into which electrical connection plugs can be inserted, the conductive material of each compartment being further connected to connection means designed to be connected to the internal electrical device;
- each compartment is adjacent to at least a part of the sealing membrane, all the compartments of the housing being arranged with respect to the sealing membrane.
- the compartments form successive layers parallel to the mean plane formed by the sealing membrane, the compartments being insulated from one another by electrically insulating and pierceable membranes.
- the conductive material is an electrically-conductive solution.
- the conductive material is an electrically-charged polymer.
- the conductive material is a mixture of conductive material powders.
- the housing comprises a circular opening forming a cylindrical cavity inside which the compartments are arranged.
- the housing comprises implantation means to allow positioning the subcutaneous device by implantation in a bone wall of the animal.
- the housing comprises alignment means to facilitate the positioning and guide the insertion of electrical connection plugs into the corresponding conductive materials.
- the alignment means comprise magnets arranged on the surface of the housing to cooperate with magnets outside the animal body.
- the system further comprises an external device designed to be connected to the external electrical device, and having electrical connection plugs in the form of penetrating pins designed to be inserted from the outside of the animal body percutaneously inside the compartments of the housing of the subcutaneous device.
- the external device further comprises alignment means to facilitate positioning and guide the insertion of electrical connection plugs into the corresponding conductive materials of the subcutaneous device housing.

the electrical connection plugs are arranged parallel in the external device, and the alignment means of the external device comprise a guiding body designed to guide the translation of said electrical connection plugs and positioning means for the guiding body with regard to the subcutaneous device.

the external device further comprises a roughly cylindrical body in which the electrical connection plugs are arranged, the guiding body having a hollow cylindrical form with an opening diameter corresponding roughly to the diameter of the external device's body.

the alignment means of the external device comprise magnets designed to cooperate with magnets positioned at the surface of the housing of the subcutaneous device.

According to another aspect of the invention, a subcutaneous device for electrical connection is proposed especially suited to the system proposed permitting a percutaneous electrical connection. More precisely, a subcutaneous device for electrical connection is proposed for the electrical connection system proposed, consisting of:

an open housing having at least one inner compartment, said compartment being filled with a conductive material into which an electrical connection plug can be inserted, the conductive material of the compartment being further connected to connection means designed to be connected to the internal electrical device;

a sealing membrane for sealing the housing, said sealing membrane being formed of an insulating and flexible material designed for insertion of electrical connection plugs from outside the housing through said sealing membrane to the conductive material of the compartment;

characterized in that the housing comprises alignment means to facilitate positioning and guide the insertion of electrical connection plugs into the corresponding conductive materials.

According to another aspect of the invention, an external device for electrical connection is proposed especially suited to the system proposed permitting a percutaneous electrical connection. More precisely, an external device for electrical connection is proposed for the proposed electrical connection system, having electrical connection plugs in the form of penetrating pins designed to be inserted from the outside of the animal body percutaneously inside the compartments of the housing of the subcutaneous device, characterized in that it further comprises alignment means for facilitating positioning and guiding the insertion of the electrical connection plugs into the corresponding conductive materials of the subcutaneous device housing.

According to still another aspect of the invention, it is proposed to use the electrical connection system proposed as an emergency electrical connector to connect a power supply source outside the animal body to an electrical implanted medical device inside the animal body and connected to the subcutaneous device.

DESCRIPTION OF THE FIGURES

Other characteristics and advantages of the invention will appear from the following description, which is purely illustrative and non-limiting and should be read with regard to the attached drawings, in which.

DETAILED DESCRIPTION OF THE INVENTION

The general principle of the percutaneous electrical connection system presented here resides in the use of a subcutaneous device for electrical connection. By subcutaneous device is meant a device that is designed to be implanted in the patient and positioned subcutaneously and which therefore includes all the means necessary for such a subcutaneous implantation, especially in terms of biocompatibility of the materials, a suitable shape for subcutaneous positioning and corresponding position maintenance, etc.

The subcutaneous electrical connection device is therefore designed to be positioned subcutaneously in the patient and is connected electrically to an internal electrical device implanted in the patient's body. As we will see in more detail below, the subcutaneous device is further designed to be connected to an external electrical device by means of electrical connection plugs in the form of penetrating pins that can be inserted through the patient's skin from outside to be inserted inside the subcutaneous device and thus permit an electrical connection between the outside and the inside of the patient's body.

Such a percutaneous electrical connection system can have various uses, of which the following examples are non-limiting illustrations.

The subcutaneous device can first be used as a main electrical connection route. In this case, the electrical connection with an external electrical device is done only when desired, for example, to recharge a battery implanted in the patient and connected to said subcutaneous device, or even to exchange data regularly between an implanted device and an external electrical device when such a data exchange does not necessarily need to be done continuously.

Another possible use consists of using the subcutaneous device as a secondary electrical connection, in particular as a backup or emergency electrical connection to compensate for a malfunction in a main electrical connection route. Such a use is particularly advantageous to replace a defective power supply route. Indeed, in the existing solutions for percutaneous electrical connection, both for transmissions by implanted cable or by use of a permanent percutaneous electrical connection, the equipment used (cables, antennas, conductors, etc.) can break down due to natural wear and tear or to accidents that could seriously disrupt the power supply to the implanted devices both with respect to the external part and the internal part of these devices. Among these malfunctions, infection or breakage of power cables can have serious consequences, threatening the patient's life. In such cases, the fact of having a subcutaneous device permitting supplying a defective implanted medical device in an emergency (only a few seconds are necessary to insert the external electrical pins into the subcutaneous housing) is particularly advantageous.

Figure 1:
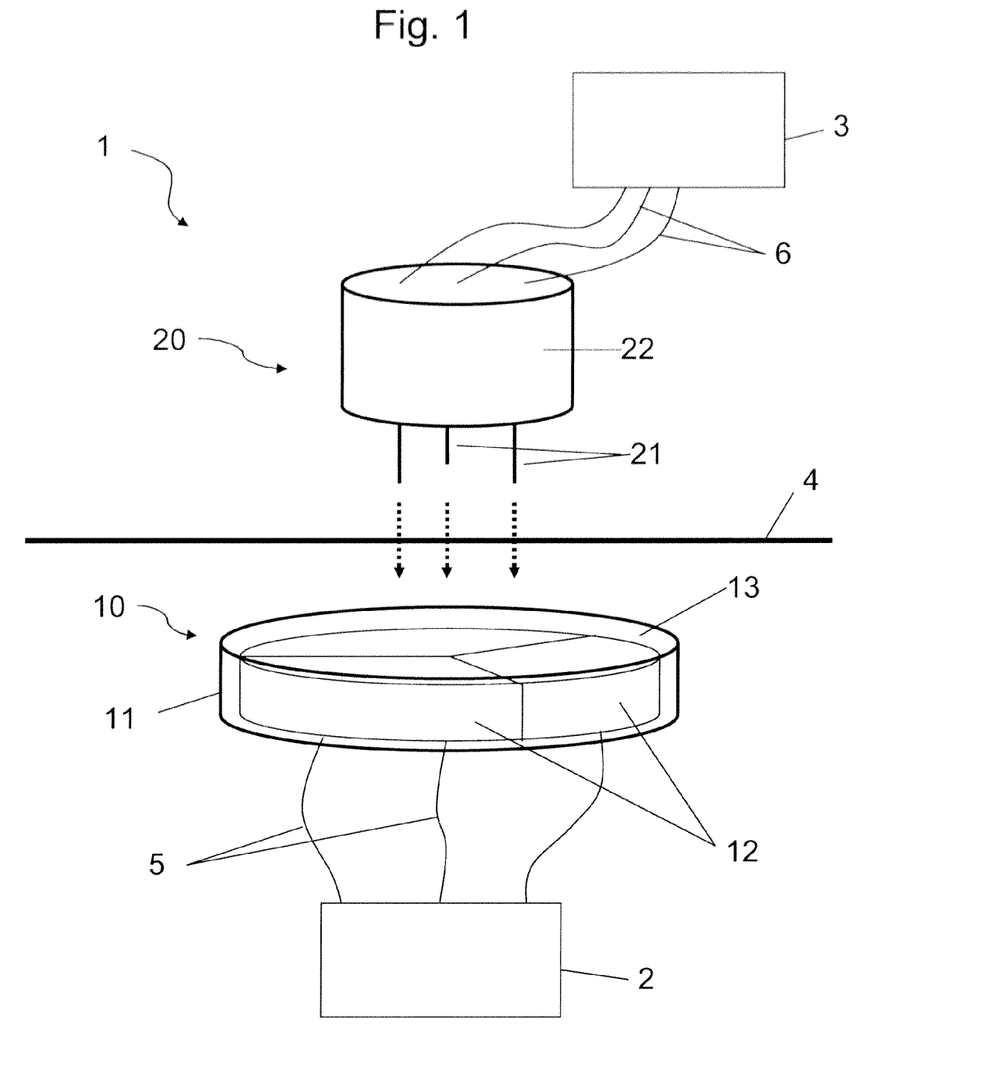
FIG. 1 is a three-dimensional schematic representation of the electrical connection system according to a first embodiment of the invention.

FIG. 1 is a schematic representation illustrating the functioning and structure of percutaneous electrical connection system 1 proposed.

Electrical connection system 1 first comprises a subcutaneous device 10 that is designed to be connected to an internal electrical device 2 implanted in the patient.

This subcutaneous device 10 has a housing 11 with a suitable form to be implanted under skin 4 without creating discomfort for the patient. This housing 11 can, for example, be in the shape of a cylinder, preferably a flat cylinder like a puck, or an oval or other form.

Furthermore, housing 11 preferably has implantation means to allow positioning subcutaneous device 10 in a bone wall of the patient.

Housing 11 is open, i.e., it has an opening between the inside and the outside of housing 11. At least one connection compartment 12 is arranged in its inner cavity, and preferably several connection compartments 12 are arranged. The compartment number is preferably equal to the number of electrical wires that one wishes to connect between the internal electrical device and the external electrical device.

The housing therefore has at least one compartment, especially if electrical connection system 1 must be used to transfer data where a single electrical wire is necessary. In this case, an electrical wire can further be connected onto the patient's skin for grounding. Preferably, housing 11 has at least two separate compartments, and preferably three separate compartments for the case of an electrical connection for a power supply for an internal electrical device. Of course, there can be more or fewer compartments if electrical connection system 1 allows data transfer in addition to power supply, or if it is used exclusively for data transfer.

The various compartments 12 provided in housing 11 are separate and electrically insulated from one another. Each compartment 12 is connected by means of connection 5 designed to be connected to internal electrical device 2. Preferably, each compartment is electrically coupled to an electrical wire 5 designed to be connected to a corresponding electrical wire of internal electrical device 2.

Each compartment 12 is further filled with a conductive material (not shown) in electrical connection with corresponding electrical wire 5. The conductive material used can have various forms and is mainly chosen for its conductive capacities, its simplicity of use and positioning in the housing, its longevity, etc.

The conductive material, for example, can have a solid form with a texture allowing penetrating pins to be inserted into said conductive material. For example, a charged polymer material, a charged gel, or even a mixture of conductive material powers (for example silver powder, titanium powder, etc.) can be used.

The conductive material can also be liquid, with a fairly substantial viscosity, in order to stay better in the housing. For example, a NaCl solution can be used.

Subcutaneous device 10 further comprises a sealing membrane 13 that seals housing 11 by ensuring a good seal between the inside and the outside of housing 11 to prevent subcutaneous device 10 from degrading.

This sealing membrane 13 is preferably formed of an insulating and flexible material designed for insertion of electrical connection plugs 21 from outside housing 11 through said flexible sealing membrane 13 to the conductive materials of compartments 12.

Preferably, this sealing membrane 13 is placed on the upper face of housing 11 which is designed to be positioned immediately under skin surface 4 of the patient.

With such a subcutaneous device 10, it is possible to electrically connect an internal electrical device 2 with an external electrical device 3 by using an external electrical connection device 20 having electrical connection plugs 21 that are designed to cross skin surface 4 of the patient and then be inserted into the conductive materials enclosed in the various compartments 12 of housing 11 by means of flexible membrane 13 positioned opposite said compartments 12 in housing 11.

Preferably, electrical connection plugs 21 are penetrating pins formed of a conductive material, and are designed to easily cross patient skin surface 4.

These connection plugs 21 are preferably positioned in a body 22 of external device 20, parallel with regard to one another. They are further connected to an external electrical device 3 by means of electrical connection means 6 (in the form of electrical wires, for example).

As indicated above, external electrical device 3 can be of any type, such as, for example, a power generator or an electrical signal sensor, percutaneous electrical system 1 proposed permitting providing the power necessary to implanted electrical device 2, or collecting electrical signals emitted by this device, in a simple manner consisting of inserting penetrating pins 21 through skin surface 4 to plant them inside subcutaneous device 10.

According to a first embodiment of the invention such as illustrated schematically in FIG. 1, compartments 12 are arranged opposite sealing membrane 13. For housing 11 having the shape of a puck, one will have compartments 12 arranged in as many sectors as there are power phases or connections necessary to capture information, for example.

It is preferable that electrical connection pins 21 be inserted perpendicularly to the mean plane defined by housing 11 (generally corresponding to the plane of membrane 13), this particular arrangement has the advantage of offering tolerance for the axis of insertion of the pins that can vary very slightly from the perpendicular, which facilitates the connection of external device 20 to subcutaneous device 10.

Figure 2:
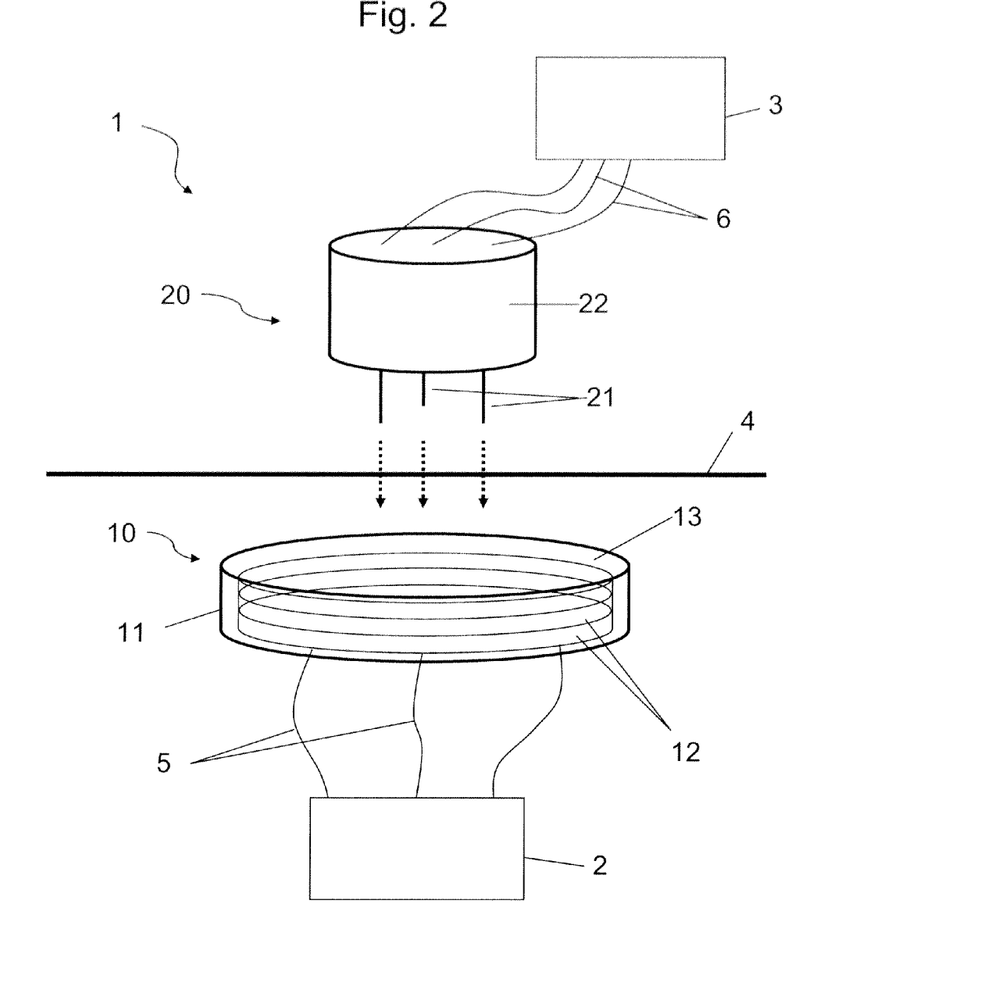
FIG. 2 is a three-dimensional schematic representation of the electrical connection system according to a second embodiment of the invention.

According to another embodiment of the invention such as illustrated schematically in FIG. 2, compartments 12 form successive layers parallel to the mean plane formed by sealing membrane 13, the compartments being insulated from one another by membranes (not shown) that are electrically insulating and pierceable by the electrical connection pins (flexible membranes). In this case, an external electrical connection device 10 is used with special electrical plugs 21. In fact, conductive pins 21 can be used of different lengths, for example, according to the position of layer 12 of conductive material to which the plug in question must be connected. Another solution is to use partially insulated conductive pins 21, also according to the position of layer 12 of conductive material to which the plug in question must be connected.

In this case, the functioning of system 1 is independent of the position of external device 20, which can be in any position at 360° around the axis of insertion of pins 21 through the skin and the insulating membrane of the subcutaneous housing, and with the condition that the axis of insertion of external device 20 and that of the conductive zone of subcutaneous device 10 are essentially aligned.

Figure 3:
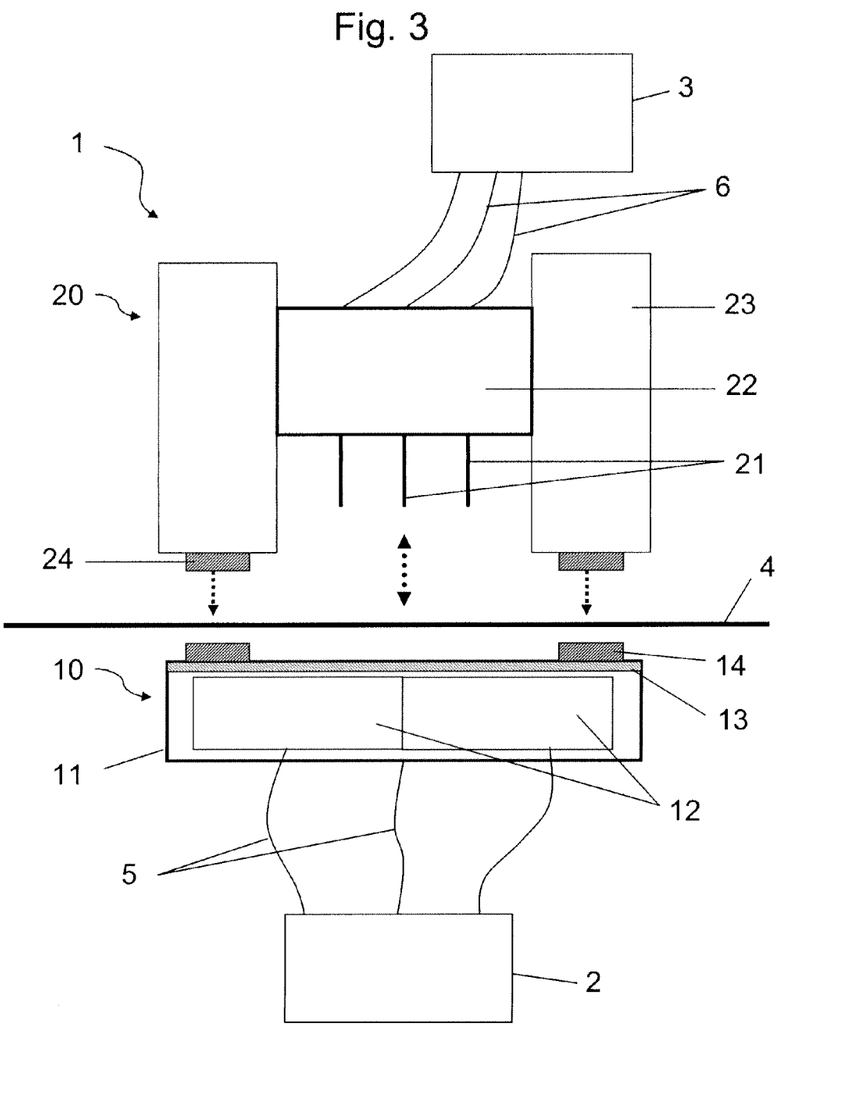
FIG. 3 is a three-dimensional schematic representation of the electrical connection system according to a third embodiment of the invention.

According to still another embodiment of the invention such as illustrated schematically in FIG. 3, percutaneous electrical connection 1 has alignment means (14, 23, 24) that allow correctly positioning external electrical connection device 20 with regard to subcutaneous device 10 positioned in the patient.

Such alignment means are designed to permit anyone, even outside the healthcare services, to position and activate the power socket so that it fulfills its function, and therefore to simplify its handling as much as possible.

To this end, alignment means can be used, for example, comprising a guiding body 23 which will permit, after having been correctly positioned with regard to subcutaneous device 10, guiding the translation of body 22 on which electrical connection pins 21 are positioned in view of insertion through skin surface 4 in the right orientation. Such a guiding body 23 has a suitable shape to cooperate with body 22 of external device 20 so as to allow translation of connection pins 21 in a single direction. Guiding body 23 and body 22 can be removable or not. External device 20 can have an essentially cylindrical body 22, for example, in which electrical connection plugs 21 are arranged, body 23 of the alignment means of external device 20 then having a hollow cylindrical shape with an opening diameter essentially corresponding to the diameter of body 22 of external device 20.

Preferably, the alignment means further comprises magnets 14 and 24 respectively positioned on housing 11 of subcutaneous device 10 and on guiding body 23 of external device 20. Thus, guiding body 23 of the socket is positioned approximately on top of subcutaneous device 10, the precise positioning being then automatically done by alignment of magnets 14 and 24 positioned respectively in housing 11 of subcutaneous device 10 and on guiding body 23 of external device 20. Once guiding body 23 is stabilized, a pressure is exerted on body 22 located in guiding body 23 to make penetrating conductive pins 21 penetrate into subcutaneous housing 11 after they have crossed skin surface 4.

In order to facilitate the positioning of external electrical connection device 20, the skin can be marked beforehand by tattooing, in order to have a more precise idea of the position of subcutaneous device 10.

It is also possible not to use the guiding body to position and insert electrical connection plugs 21, in which case, the position and orientation of subcutaneous device are manually identified, by palpation, for example.

According to one particular example, percutaneous electrical connection system 1 presented is used as a backup electrical connection for a heart pump, like an implanted left ventricular assist device (LVAD), which requires a necessarily continuous power supply.

In this case, electrical implanted medical device 2, i.e., the heart assist pump, is, for example, connected to a main power supply cable, by means of a particular electrical connection device that allows connecting a second power supply cable parallel to the main power supply cable, to the end of which is connected subcutaneous electrical connection device 10. Thus, when the main power supply cable is broken, it is possible to connect a second power supply source to implanted electrical medical device 2 by means of subcutaneous device 10 connected to the second power supply cable and to the electrical connection device. With such an arrangement, it is therefore possible to cut the main power supply of implanted electrical device 2 while continuing to supply the heart assist pump with power by means of electrical connection subcutaneous device 10 coupled to a power source via external electrical connection device 20, thus guaranteeing the continuous operation of the heart assist pump. Such an arrangement therefore allows routinely giving cardiac assists a backup power socket, just like a spare tire for a vehicle.

The subcutaneous device can therefore act as a backup socket, called "LS (Life Safety) socket" or "AEEC (Additional Emergency Electrical Connection) socket", which can be used for any type of implanted medical device to ensure the patient's life.

The reader will understand that numerous modifications can be introduced without materially exceeding the scope of the novel teachings and advantages described here. Consequently, all modifications of this type are intended to be incorporated into the scope of the electrical connection system according to the invention.

The invention claimed is:

1. An electrical connection system for a percutaneous electrical connection between an electrical device (2) inside an animal body and an electrical device (3) outside said body, comprising a subcutaneous device (10) designed to be connected to internal electrical device (2), said subcutaneous device (10) comprising:
    an open housing (11) having at least one inner compartment (12), said compartment (12) being filled with a conductive material into which an electrical connection plug can be inserted, the conductive material of compartment (12) being further connected to connection means (5) designed to be connected to internal electrical device (2);
    a sealing membrane (13) for sealing housing (11), said sealing membrane ( )) being formed of an insulating and flexible material designed for insertion of electrical connection plugs from outside housing (11) through said sealing membrane (13) to the conductive material of compartment (12);
    wherein housing (11) comprises alignment means (14) to facilitate positioning and to guide the insertion of electrical connection plugs into the corresponding conductive materials.

2. The system of claim 1, wherein housing (11) comprises several inner compartments (12) insulated electrically from one another, each compartment (12) being filled with a conductive material into which an electrical connection plug can be inserted, the conductive material of each compartment (12) being further connected to connection means (5) designed to be connected to internal electrical device (2).

3. The system of claim 2, wherein each compartment (12) is adjacent to at least a part of sealing membrane (13), all the compartments (12) of housing (11) thus facing sealing membrane (13).

4. The system of claim 2, wherein compartments (12) form successive layers parallel to the mean plane formed by sealing membrane (13), the compartments (12) being insulated from one another by electrically insulating and pierceable membranes.

5. The system of claim 1, wherein the conductive material is an electrically-conductive solution.

6. The system of claim 1, wherein the conductive material is an electrically-charged polymer.

7. The system of claim 1, wherein the conductive material is a mixture of conductive material powders.

8. The system of claim 1, wherein housing (11) comprises a circular opening forming a cylindrical cavity inside of which compartment or compartments (12) are arranged.

9. The system of claim 1, wherein housing (11) comprises implantation means to enable positioning of the subcutaneous device (10) by implantation in a bone wall of the animal.

10. The system of claim 1, wherein alignment means (14) comprise magnets arranged on the surface of housing (11) to cooperate with magnets outside the animal body.

11. The system of claim 1, further comprising an external device (20) designed to be connected to external electrical device (3), and having electrical connection plugs (21) in the form of penetrating pins designed to be inserted from the outside of the animal body percutaneously inside compartments (12) of housing (11) of subcutaneous device (10).

12. The system of claim 11, wherein external device (20) further comprises alignment means (23,24) to facilitate positioning and guide the insertion of electrical connection plugs (21) into the corresponding conductive materials of housing (11) of subcutaneous device (10).

13. The system of claim 12, wherein electrical connection plugs (21) are arranged parallel in external device (20), and in that the alignment means of the external device comprise a guiding body (23) designed to guide the translation of said electrical connection plugs (21) and positioning means for guiding body (23) with regard to subcutaneous device (10).

14. The system of claim 13, wherein external device (20) further comprises a roughly cylindrical body (22) in which electrical connection plugs (21) are arranged, the guiding body (23) having a hollow cylindrical form with an opening diameter corresponding roughly to the diameter of body (22) of external device (20).

15. The system of claim 12 taken in combination with claim 10, wherein the alignment means for external device (20) comprise magnets (24) designed to cooperate with magnets (14) positioned at the surface of housing (11) of subcutaneous device (10).

16. A subcutaneous device (10) for electrical connection for the electrical connection system (1) of claim 1, comprising:
- an open housing (11) having at least one inner compartment (12), said compartment (12) being filled with a conductive material into which an electrical connection plug can be inserted, the conductive material of compartment (12) being further connected to connection means (5) designed to be connected to internal electrical device (2);
- a sealing membrane (13) for sealing housing (11), said sealing membrane (13) being formed of an insulating and flexible material designed for insertion of electrical connection plugs from outside housing (11) through said sealing membrane (13) to the conductive material of compartment (12);
- wherein housing (11) comprises alignment means (14) to facilitate positioning and guide the insertion of electrical connection plugs into the corresponding conductive materials.

17. An external device (20) for the electrical connection system (1) of claim 1, having electrical connection plugs (21) in the form of penetrating pins designed to be inserted from the outside of the animal body percutaneously inside compartments (12) of housing (11) of subcutaneous device (10), wherein it further comprises alignment means (23, 24) for facilitating positioning and guiding the insertion of the electrical connection plugs (21) into corresponding conductive materials (11) of subcutaneous device housing (10).

18. Use of the electrical connection system (1) of claim 1 as an emergency electrical connector to connect a power supply source outside the animal body to an electrical implanted medical device inside the animal body and connected to the subcutaneous device.

* * * * *

UNITED STATES PATENT AND TRADEMARK OFFICE
CERTIFICATE OF CORRECTION

PATENT NO. : 8,545,255 B2
APPLICATION NO. : 13/265838
DATED : October 1, 2013
INVENTOR(S) : Pierre-Yves Litzler et al.

Page 1 of 1

It is certified that error appears in the above-identified patent and that said Letters Patent is hereby corrected as shown below:

In the Claims

Column 8, Claim 1, line 12, please delete "())" and insert --(13)--.

Column 8, Claim 12, line 60, please delete "(23,24)" and insert --(23, 24)--.

Signed and Sealed this
Seventeenth Day of June, 2014

Michelle K. Lee
*Deputy Director of the United States Patent and Trademark Office*